United States Patent
Cao et al.

(10) Patent No.: US 11,304,926 B2
(45) Date of Patent: Apr. 19, 2022

(54) APPLICATION OF TRANSIENT RECEPTOR POTENTIAL CATION CHANNEL TRPV3 IN DEVELOPING DRUG FOR PREVENTING OR TREATING PSORIASIS

(71) Applicant: CHINA PHARMACEUTICAL UNIVERSITY, Nanjing (CN)

(72) Inventors: Zhengyu Cao, Nanjing (CN); Yujing Wang, Nanjing (CN); Zhiqi Yin, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 90 days.

(21) Appl. No.: 16/849,555

(22) Filed: Apr. 15, 2020

(65) Prior Publication Data
US 2020/0246305 A1    Aug. 6, 2020

Related U.S. Application Data

(63) Continuation of application No. PCT/CN2019/070763, filed on Jan. 8, 2019.

(51) Int. Cl.
*A61P 17/06* (2006.01)
*A61K 31/352* (2006.01)

(52) U.S. Cl.
CPC .......... *A61K 31/352* (2013.01); *A61P 17/06* (2018.01)

(58) Field of Classification Search
CPC ........ A61K 31/352; A61K 45/00; A61P 17/06
USPC ........................................... 514/456
See application file for complete search history.

(56) References Cited

U.S. PATENT DOCUMENTS

| | | | |
|---|---|---|---|
| 2003/0105031 A1* | 6/2003 | Rosenbloom | A61K 36/736 514/27 |
| 2011/0144135 A1* | 6/2011 | Chong | A61P 25/06 514/262.1 |

OTHER PUBLICATIONS

Wikipedia , Psoriasis, Apr. 2017, p. 1-13 (Year: 2017).*

* cited by examiner

*Primary Examiner* — Taylor V Oh
(74) *Attorney, Agent, or Firm* — CBM Patent Consulting, LLC

(57) ABSTRACT

A pathophysiological effect of a transient receptor potential cation channel, subfamily V, member 3 (TRPV3) on psoriasis, which can be used to develop a drug for preventing or treating psoriasis. The invention further discloses an application of Scutellarein as a TRPV3 inhibitor in preparing a drug for preventing or treating psoriasis. When a drug containing the TRPV3 inhibitor discovered according to the invention or provided by the invention is used for preventing or treating psoriasis, good prevention or treatment effects can be achieved.

2 Claims, 9 Drawing Sheets

Specification includes a Sequence Listing.

FIG. 3A
FIG. 3B
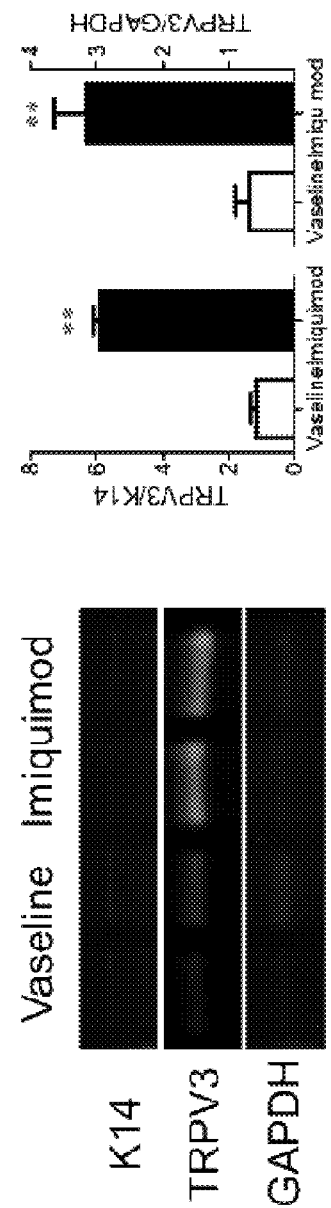
FIG. 3C
FIG. 3D

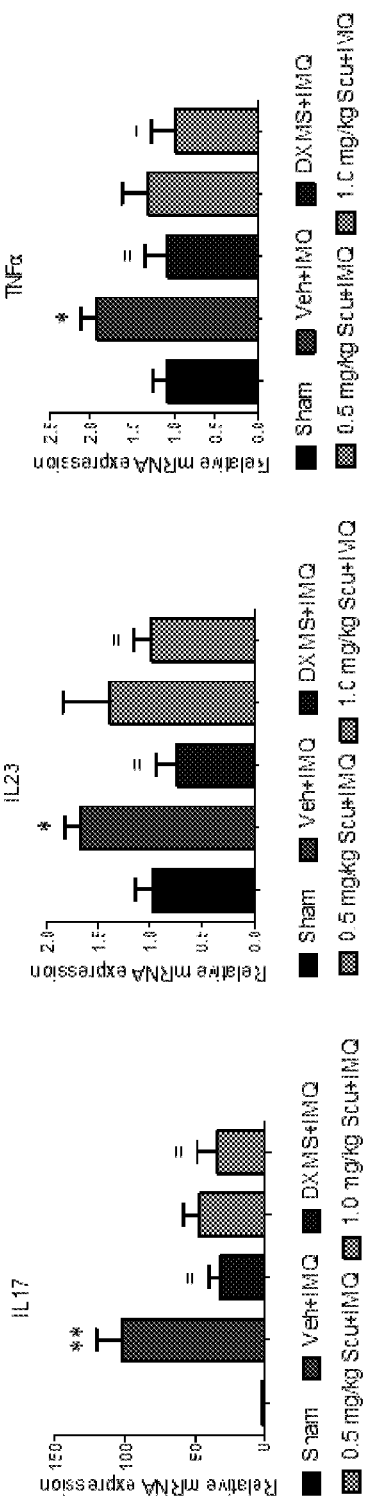

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: It is synthesized.

<400> SEQUENCE: 1
cggtcaccaa gacctctcca           20

<210> SEQ ID NO 2
<211> LENGTH: 20
<212> TYPE: DNA
<213> ORGANISM: Artificial Sequence
<220> FEATURE:
<223> OTHER INFORMATION: It is synthesized

<400> SEQUENCE: 2
cgctcggact gttgggattg           20

```
<210> SEQ ID NO 3
<211> LENGTH: 19
<212> TYPE: DNA
<213> ORGANISM: Artificial Sequence
<220> FEATURE:
<223> OTHER INFORMATION: It is synthesized.

<400> SEQUENCE: 3
gtgtgaaagc agcaaagag                                                 19

<210> SEQ ID NO 4
<211> LENGTH: 19
<212> TYPE: DNA
<213> ORGANISM: Artificial Sequence
<220> FEATURE:
<223> OTHER INFORMATION: It is synthesized.

<400> SEQUENCE: 4
ctccaaaaga ccagtgatg                                                 19

<210> SEQ ID NO 5
<211> LENGTH: 20
<212> TYPE: DNA
<213> ORGANISM: Artificial Sequence
<220> FEATURE:
<223> OTHER INFORMATION: It is synthesized.

<400> SEQUENCE: 5
gtccttgttc cactgtgcct                                                20

<210> SEQ ID NO 6
<211> LENGTH: 20
<212> TYPE: DNA
<213> ORGANISM: Artificial Sequence
<220> FEATURE:
<223> OTHER INFORMATION: It is synthesized.

<400> SEQUENCE: 6
gcttccacat gtcctcacaa                                                20

<210> SEQ ID NO 7
<211> LENGTH: 99
<212> TYPE: DNA
<213> ORGANISM: Artificial Sequence
<220> FEATURE:
<223> OTHER INFORMATION: It is synthesized.

<400> SEQUENCE: 7
ggactgcagt tcctatggca gcttcagcga cgcggtgctg gagctcttca agctcaccat    60
aggcctgggc gacctgaaca tccagcagaa ctccaccta                          99

<210> SEQ ID NO 8
<211> LENGTH: 56
<212> TYPE: DNA
<213> ORGANISM: Artificial Sequence
<220> FEATURE:
<223> OTHER INFORMATION: It is synthesized.

<400> SEQUENCE: 8
ggactgcagt tccttcagcg acgcggcgac ctgaacatcc agcagaactc caccta        56

<210> SEQ ID NO 9
<211> LENGTH: 21
<212> TYPE: DNA
<213> ORGANISM: Artificial Sequence
<220> FEATURE:
```

<223> OTHER INFORMATION: It is synthesized

<400> SEQUENCE: 9
tttaactccc ttggcgcaaa a                                                 21

<210> SEQ ID NO 10
<211> LENGTH: 20
<212> TYPE: DNA
<213> ORGANISM: Artificial Sequence
<220> FEATURE:
<223> OTHER INFORMATION: It is synthesized.

<400> SEQUENCE: 10
ctttccctcc gcattgacac                                                   20

<210> SEQ ID NO 11
<211> LENGTH: 21
<212> TYPE: DNA
<213> ORGANISM: Artificial Sequence
<220> FEATURE:
<223> OTHER INFORMATION: It is synthesized.

<400> SEQUENCE: 11
atgctggatt gcagagcagt a                                                 21

<210> SEQ ID NO 12
<211> LENGTH: 23
<212> TYPE: DNA
<213> ORGANISM: Artificial Sequence
<220> FEATURE:
<223> OTHER INFORMATION: It is synthesized.

<400> SEQUENCE: 12
acggggcaca ttatttttag tct                                               23

<210> SEQ ID NO 13
<211> LENGTH: 22
<212> TYPE: DNA
<213> ORGANISM: Artificial Sequence
<220> FEATURE:
<223> OTHER INFORMATION: It is synthesized.

<400> SEQUENCE: 13
tcgagaccat ttactgcaac ag                                                22

<210> SEQ ID NO 14
<211> LENGTH: 21
<212> TYPE: DNA
<213> ORGANISM: Artificial Sequence
<220> FEATURE:
<223> OTHER INFORMATION: It is synthesized.

<400> SEQUENCE: 14
cattgccggt ggaaattcct t                                                 21

<210> SEQ ID NO 15
<211> LENGTH: 19
<212> TYPE: DNA
<213> ORGANISM: Artificial Sequence
<220> FEATURE:
<223> OTHER INFORMATION: It is synthesized.

<400> SEQUENCE: 15
cctgtagccc acgtcgtag                                                    19

<210> SEQ ID NO 16
<211> LENGTH: 22
<212> TYPE: DNA
<213> ORGANISM: Artificial Sequence
<220> FEATURE:
<223> OTHER INFORMATION: It is synthesized.

<400> SEQUENCE: 16
gggagtagac aaggtacaac cc                                              22

<210> SEQ ID NO 17
<211> LENGTH: 20
<212> TYPE: DNA
<213> ORGANISM: Artificial Sequence
<220> FEATURE:
<223> OTHER INFORMATION: It is synthesized.

<400> SEQUENCE: 17
ctccacttgc agcctttacc                                                 20

<210> SEQ ID NO 18
<211> LENGTH: 23
<212> TYPE: DNA
<213> ORGANISM: Artificial Sequence
<220> FEATURE:
<223> OTHER INFORMATION: It is synthesized.

<400> SEQUENCE: 18
ttcatcttgc tggttcttcg tct                                             23

<210> SEQ ID NO 19
<211> LENGTH: 22
<212> TYPE: DNA
<213> ORGANISM: Artificial Sequence
<220> FEATURE:
<223> OTHER INFORMATION: It is synthesized.

<400> SEQUENCE: 19
gactcttgcg tcaacttcaa gg                                              22

<210> SEQ ID NO 20
<211> LENGTH: 21
<212> TYPE: DNA
<213> ORGANISM: Artificial Sequence
<220> FEATURE:
<223> OTHER INFORMATION: It is synthesized.

<400> SEQUENCE: 20
caggctgtct tttgtcaacg a                                               21

APPLICATION OF TRANSIENT RECEPTOR POTENTIAL CATION CHANNEL TRPV3 IN DEVELOPING DRUG FOR PREVENTING OR TREATING PSORIASIS

This application is the continuation application of International Application No. PCT/CN2019/070763 filed on 8 Jan. 2019 which claims priority to Chinese Application No. CN201810284657.3 filed on 2 Apr. 2018, the entire contents of each of which are hereby incorporated by reference.

TECHNICAL FIELD

The present invention relates to the field of medicine, and more particularly, to an application of a TRPV3 inhibitor in developing a drug for preventing or treating psoriasis and an application of Scutellarein as a TRPV3 inhibitor in a drug for treating psoriasis and relative diseases caused by function enhancement/expression increase of a TRPV3.

BACKGROUND

Psoriasis is a common cutaneous inflammatory disease, characterized by erythema and scale. The psoriasis affects 2% to 3% of the world's population. According to clinical features, the psoriasis may be divided into psoriasis vulgaris, psoriatic arthritis, pustular psoriasis and psoriatic erythroderma. And more than 90% of the psoriasis belongs to the psoriasis vulgaris. Psoriatic plaques may occur on multiple parts of a body and are typically red or salmon pink in color, covered by white or silvery scales. Considering that the psoriasis has a long course of disease, is easy to relapse and difficult to be radically cured, and frequently causes damages to patients' appearances, patients are subjected to greater impacts on physical health and mental status from the psoriasis.

Therapeutic purposes of the psoriasis include controlling a disease condition, relieving symptoms, avoiding recurrence and improving a life quality of the patients. Regarding to the treatments of the psoriasis, tazarotene (tretinoin), intermediate-acting and strong glucocorticoid, and calcipotriol are used as first-line external drugs for local treatment; the aforementioned local treatment may be combined with photochemotherapy, including UVA, PUVA, broad spectrum UVB and narrow spectrum UVB, according to the type of the psoriasis. Meanwhile, the patients may receive orally administered drugs such as an anti-infection drug, methotrexate, cyclosporine or a biological agent (etanercept) and the like alternatively, coordinated with psychological treatment. Although there is a great diversity of treatment methods at current, some drugs or treatment methods that produce adverse responses are unavoidable. For example, abuse of glucocorticoids for pursuing therapeutic effects may lead to aggravation of skin lesions after drug withdrawal, and long-term external application of the glucocorticoids may lead to skin atrophy, barrier function damage, etc. Long-term photochemotherapy is easy to cause skin aging, pigmentation and skin cancer. A major adverse response of orally administered cyclosporines is nephrotoxicity, while orally administered tretinoins may result in sclerotin changes to the patient. Therefore, it is of great significance to find a novel effect target for treating the psoriasis and to develop a novel drug for the novel target that can relieve a disease condition and can be used for a long time without any side effects.

Currently, the psoriasis is understood as an autoimmune inflammatory disease, and abnormal proliferation of keratinocytes caused by various inflammatory factors plays a key role in disease development. Skin keratinocytes are not only responders of inflammation, but also accelerators of inflammation. A variety of ion channels widely distributed on the skin keratinocytes participate in epidermal differentiation and proliferation, skin regeneration and immune response. Transient receptor potential cation channels (TRP) refer to a kind of important non-selective cation channel superfamily located on cell membranes and expressed in almost all cells of human organs. The TRP channels are divided into six subfamilies including a TRPC (Cannonical, TRPC1-7), a TRPV (Vanilloid, TRPV1-6), a TRPM (Melastatin, TRPM1-8), a TRPP (Polycystin, TRPP2, TRPP3, TRPP5), a TRPML (Mucolipin, TRPML1-3) and a TRPA (Ankyrin, TRPA1). These channels are related to such functions including a visual sense, an auditory sense, an olfactory sense, a gustatory sense and a somatic sense (such as a sense of pain, mechanical irritation, temperature sensation, etc.). Temperature-sensitive transient receptor potential channels include a TRPV1, a TRPV2, a TRPV3, a TRPV4, a TRPM8 and a TRPA1, which are expressed on skin sensory neurons of skin for sensing a change in external temperature, while the TRPV1 and the TRPV3 are highly expressed in keratinocytes and may be related to skin inflammation and skin barrier formation.

SUMMARY

Aiming at the defects of the prior art, the present invention provides an application of screening a drug for preventing or treating psoriasis with a TRPV3 as a target.

In order to achieve the objective above, the present invention provides an evidence of using the TRPV3 as a drug target for preventing or treating psoriasis. The present invention shows through studies that expression and (or) activity of the TRPV3 is increased in skin inflammation, and deletion of the TRPV3 can relieve a psoriasis-like lesion of a mouse induced by imiquimod. In order to achieve the objective above, the present invention further provides a novel TRPV3 inhibitor—Scutellarein. The present invention shows through studies that the Scutellarein can inhibit the activity of the TRPV3, and can relieve the psoriasis-like lesion of the mouse induced by the imiquimod.

Specific technical solutions of the present invention are as follows.

An application of a transient receptor potential cation channel TRPV3 in developing a drug for preventing or treating psoriasis is provided.

The TRPV3 is used as a drug target in the application above to observe expression and/or activity of the TRPV3 in skin inflammation reduced by a drug.

Further, the drug is a TRPV3 inhibitor. The TRPV3 inhibitor includes one or more of psoriasis vulgaris, pustular psoriasis, psoriatic erythroderma and psoriatic arthritis.

Further, the drug is screened and verified by a cell line overexpressing the TRPV3. Preferably, the cell line overexpressing the TRPV3 includes a tool cell obtained by plasmid transfection or virus infection that stably expresses the TRPV3.

The present invention provides a high-throughput screening method for screening and identifying a TRPV3 inhibitor, which uses a cell line overexpressing a TRPV3 to screen and identify a drug inhibiting intracellular calcium increase induced by 2-aminoethoxybiphenylborate (2-APB) through a fluorescent probe specifically bound to calcium.

Another objective of the present invention is to provide an application of scutellarin and a stereoisomer thereof, as well as a pharmaceutically acceptable salt and/or a solvate thereof in preparing a transient receptor potential cation channel TRPV3 inhibitor, wherein the scutellarin has a structure of formula (1).

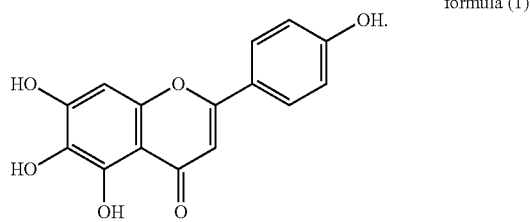

formula (1)

The transient receptor potential cation channel TRPV3 inhibitor above is used for preventing or treating related diseases caused by function enhancement/expression increase of the TRPV3. Preferably, the disease is psoriasis.

The disease according to the present invention is psoriasis, including one or more of psoriasis vulgaris, pustular psoriasis, psoriatic erythroderma and psoriatic arthritis.

A method for preparing the Scutellarein of the present invention is not particularly limited, and those skilled in the art can prepare the Scutellarein of the present invention according to the common sense in the art, or obtain the Scutellarein of the present invention from market. Preferably, the Scutellarein of the present invention can be prepared according to a method provided in Literature (Jingbing Wen, Qingwen Zhang, Zhiqi Yin, et al. Study on Chemical Components of Flavonoids in Oroxylum Indicum Seeds [J]. Chinese Pharmaceutical Journal, 2011, 46(3):170-173).

The stereoisomer of the Scutellarein of the present invention is not particularly limited and may be a conventional choice in the art. For example, the stereoisomer of the Scutellarein may be an enantiomer or a diastereomer of the Scutellarein. In addition, the pharmaceutically acceptable salt is not particularly limited in the present invention, and may be a conventional choice in the art.

Further, the solvate is not particularly limited in the present invention either, and may be a conventional choice in the art. Preferably, the solvate includes dissolving the Scutellarein in one or more of dimethyl sulfoxide, Tween 80, normal saline, hydrochloric acid and ethyl alcohol, preferably the dimethyl sulfoxide, the Tween 80 or the normal saline.

Further, the transient receptor potential cation channel TRPV3 inhibitor also includes a pharmaceutically acceptable carrier. A dosage form of the TRPV3 inhibitor is not particularly limited as long as the TRPV3 inhibitor is convenient to use and can obtain a better therapeutic effect. Preferably, the drug may be one or more of subcutaneous injection, intradermal injection, spray, dry powder inhalation, topical solution, lotion, liniment, ointment, plaster, paste and patch, and is further preferably subcutaneous injection or ointment. When the drug is used in the dosage form above, the drug may also include excipient, stabilizing agent, preserving agent, buffer, cosolvent, emulsifier, diluent or isotonic agent.

In the present invention, methods for preparing the subcutaneous injection, the intradermal injection, the spray, the dry powder inhalation, the topical solution, the lotion, the liniment, the ointment, the plaster, the paste and the patch above are not particularly limited, and may be methods known by those skilled in the art, which will not be repeatedly elaborated here.

In the present invention, a content of the Scutellarein in the TRPV3 inhibitor is not particularly limited, and may be a conventional choice in the art as long as a good therapeutic effect can be obtained, for example, a mass percentage content of the Scutellarein may range from 0.1% to 5%.

Advantages of the present invention:

(1) In the present invention, the transient receptor potential cation channel TRPV3 inhibitor is taken as the drug target for preventing or treating psoriasis, providing a new idea of preventing or treating psoriasis.

(2) The cell line overexpressing the TRPV3 according to the present invention can be used to conveniently screen and identify the TRPV3 inhibitor, realizing a high accuracy.

(3) The present invention finds through studies that the Scutellarein and the stereoisomer thereof, as well as the pharmaceutically acceptable salt and/or the solvate thereof can effectively inhibit the transient receptor potential cation channel TRPV3, and have a good prevention or treatment effect on psoriasis, and have the advantages of convenient administration, small side effect, low toxicity and high bioavailability. Further, it can be seen from the study results provided by the present invention that: the expression of the TRPV3 is enhanced in a psoriasis lesion of a mouse induced by 5% imiquimod (IMQ), and function deletion of the TRPV3 can improve the psoriasis-like lesion of the mouse induced by IMQ; and an HEK-293 cell line overexpressing the TRPV3 obtained by liposome transfection can make a response to the 2-APB, while the screened Scutellarein has an obvious inhibitory effect on calcium influx induced by the 2-APB and a current thereof, and $IC_{50}=1.01$ μM. The Scutellarein can significantly relieve the psoriasis-like lesion of the mouse induced by 5% IMQ.

To sum up, to apply the discovery of using the TRPV3 according to the present invention as the target to prepare the drug for preventing or treating psoriasis has a good development prospect. Other characteristics and advantages of the present invention will be described in detail in the following detailed embodiments.

BRIEF DESCRIPTION OF THE DRAWINGS

The drawings constituting a part of the description are provided to further understand the present invention, and are used together with the following detailed embodiments to explain the present invention, but are not intended to limit the present invention. In the drawings:

FIG. 3A shows TRPV3 and Keratin 14 (K14) immunofluorescence staining of lesion of mouse psoriasis model induced by 5% IMQ according to a preferred embodiment provided by the present invention;

FIG. 3B shows TRPV3 mRNA expression of lesion of the mouse psoriasis model induced by 5% IMQ;

FIG. 3C shows protein expression of the TRPV3, the K14 and GAPDH at the lesion of the mouse psoriasis model induced by 5% IMQ;

FIG. 3D shows a quantitative graph of protein level of the TRPV3 at the lesion of the mouse psoriasis model induced by 5% IMQ;

FIGS. 9A to 9E show effects of Scutellarein on mRNA changes of IL17, IL23, TNFα, IL18 and CXCL15 at a lesion part of a mouse psoriasis model induced by IMQ according to a preferred embodiment provided by the present invention;

FIG. 9A shows effects of Scutellarein on mRNA changes of IL17 at a lesion part of a mouse psoriasis model induced by IMQ according to a preferred embodiment provided by the present invention;

FIG. 9B shows effects of Scutellarein on mRNA changes of IL23 at a lesion part of a mouse psoriasis model induced by IMQ according to a preferred embodiment provided by the present invention;

FIG. 9C shows effects of Scutellarein on mRNA changes of TNFα at a lesion part of a mouse psoriasis model induced by IMQ according to a preferred embodiment provided by the present invention;

FIG. 9D shows effects of Scutellarein on mRNA changes of IL18 at a lesion part of a mouse psoriasis model induced by IMQ according to a preferred embodiment provided by the present invention;

FIG. 9E shows effects of Scutellarein on mRNA changes of CXCL15 at a lesion part of a mouse psoriasis model induced by IMQ according to a preferred embodiment provided by the present invention;

FIG. 9F shows an effect of the Scutellarein on release of the CXCL15 at the lesion part of the mouse psoriasis model induced by IMQ;

DETAILED DESCRIPTION

Figure 1A:
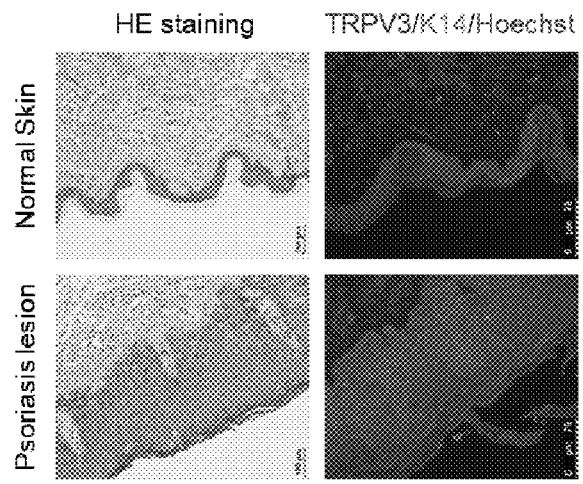
FIG. 1A shows typical HE staining and TRPV3 and Keratin 14 (K14) immunofluorescence staining of a human psoriasis lesion paraffin section and a normal skin paraffin section according to an embodiment provided by the present invention.

The specific embodiments of the present invention are described in detail hereinafter with reference to the drawings. It should be understood that the specific embodiments described here are only used for describing and explaining the present invention, but are not intended to limit the present invention.

The present invention provides an application of developing a drug for preventing or treating psoriasis with a TRPV3 as a target, and the psoriasis includes one or more of psoriasis vulgaris, pustular psoriasis, psoriatic erythroderma and psoriatic arthritis. The present invention further provides an application of Scutellarein as a TRPV3 inhibitor in preparing a drug for preventing or treating psoriasis. When a drug containing the TRPV3 inhibitor discovered according to the present invention or provided by the present invention is used for preventing or treating psoriasis, good prevention or treatment effects can be achieved. The Scutellarein is a compound of formula (1).

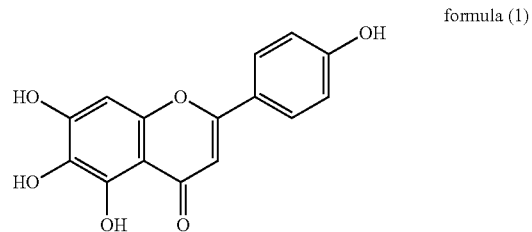 [SMILES: O=c1cc(-c2ccc(O)cc2)oc2cc(O)c(O)c(O)c12]

formula (1)

The present invention will be described in detail hereinafter with reference to the embodiments.

In the following embodiments, various reagents and materials used are commercially available unless otherwise specified.

In the following preferred embodiments, a human psoriasis lesion paraffin section and a normal skin paraffin section are provided by the Institute of Dermatology of Chinese Academy of Medical Sciences.

In the following preferred embodiments, immunofluorescence (IF) is used to locate a target protein in skin and analyze an expression level of the target protein.

In the following preferred embodiments, 5% imiquimod (IMQ) is applied continuously to induce a mouse psoriasis model to evaluate an effect of a drug on psoriasis. A psoriasis model induced by IMQ is currently a most widely used model to evaluate an effect of a drug on a process of psoriasis.

In the following preferred embodiments, experimental C57BL/6 mice and TRPV3 knockout mice (TRPV3$^{-/-}$) used are all purchased from the Experimental Animal Center of Nanjing Medical University, with half male and half female, wherein weights of the mice range from 18 g to 20 g, and ages of the mice range from 6 weeks to 8 weeks.

In the following preferred embodiments, Psoriasis Area and Severity Index (PASI) scoring standard is used to evaluate the mouse psoriasis model. The PASI scoring is a commonly used method for evaluating a severity of psoriasis in clinical tests.

In the following preferred embodiments, a skin paraffin section of a mouse is stained by a hematoxylin-eosin (HE) staining method, and subjected to pathological examination.

In the following embodiments, an expression level of a specific gene in a tissue or a cell is detected by a Western Blotting experiment.

In the following embodiments, a transcription level of a specific gene in a tissue is detected by a real-time quantitative PCR experiment.

In the following embodiments, a content of a specific protein in a tissue is detected by an enzyme-linked immunosorbent assay (ELISA) experiment.

In the following embodiments, a plasmid encoding a TRPV3 channel is transfected by a liposome to stably express the TRPV3 channel in a HEK-293 cell.

In the following embodiments, a TRPV3 inhibitor is found to inhibit intracellular calcium increase in a HEK-293 cell stably expressing the TRPV3 by high-throughput detection, and a patch clamp amplification system (HEKA Company) is used to further detect an inhibitory effect of a drug on the TRPV3 channel.

In the following embodiments, the Scutellarein used is prepared according to methods provided in Literature (Jingbing Wen, Qingwen Zhang, Zhiqi Yin, et al. Study on Chemical Components of Flavonoids in Oroxylum Indicum Seeds [J]. Chinese Pharmaceutical Journal, 2011, 46(3):170-173).

In the following preferred embodiments, an effect of the Scutellarein on the mouse psoriasis model induced by IMQ is evaluated by appearance evaluation, a pathological change, an mRNA level and a content of an inflammatory factor in skin, inflammatory cell infiltration and other indicators.

Embodiment 1

The embodiment is used to illustrate an application of developing a drug for preventing or treating psoriasis with a TRPV3 as a target provided by the present invention.

(1) HE Staining on a Human Psoriasis Lesion Paraffin Section and a Normal Skin Paraffin Section Skin tissue paraffin sections were provided by the Institute of Dermatology of the Chinese Academy of Medical Sciences and subjected to HE staining. An Eclipse Ti inverted microscope (Nikon Corporation, Tokyo, Japan) was used to observe and take a photo at 400-times magnification, and NIS-element BR software (Nikon Corporation, Tokyo, Japan) was used to measure an epidermal thickness of the skin. Six fields were randomly selected for each section. Results were shown in FIG. 1A. In human psoriasis lesion, a stratum spinosum of the skin was significantly thickened, astratum granulosum of the skin was broken or disappeared, and a stratum corneum of the skin was excessively keratinized.

Figure 1B:
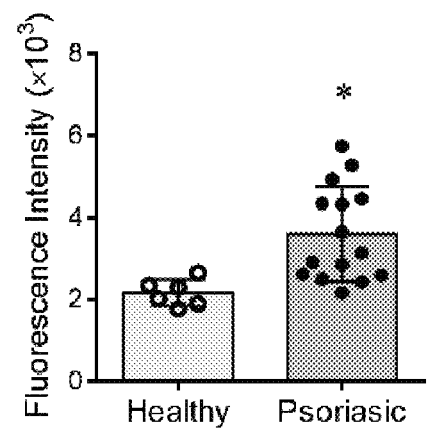
FIG. 1B shows fluorescence intensity of TRPV3 in an epidermal layer of the human psoriasis lesion paraffin section and the normal skin paraffin section.

(2) Immunofluorescence Staining on the Human Psoriasis Lesion Paraffin Section and the Normal Skin Paraffin Section An immunofluorescence staining technology was used underlying an antigen-antibody reaction to locate an antigen substance in a tissue or a cell, and a Leica microsystem analysis application was further used to measure a mean fluorescence intensity. The paraffin section was deparaffined to water, and then placed in a citrate buffer (pH=6.0) for microwave boiling to perform antigen thermal remediation. After being naturally cooled to room temperature, the paraffin section was blocked with 5% BSA at room temperature for 1 hour, then dropwise added with primary antibodies of TRPV3 and K14 diluted in PBST, incubated at 4° C. overnight, and then rinsed with PBST 3 times for 5 minutes each time. Then, a fluorescence secondary antibody diluted in PBST was dropwise added, incubated at room temperature for 1 hour, and then the section was rinsed with PBST 3 times for 5 minutes each time. Hoechst diluted in PBST was dropwise added to mark a cell nucleus, then the section was incubated at room temperature for 15 minutes, and then rinsed with PBST once. An anti-fluorescence quenching reagent was dropwise added to the section, and then the section was sealed. The section was observed and photographed under a fluorescence microscope, and a representative immunofluorescence staining image was shown in FIG. 1A, wherein K14 was a marker of a skin keratinocyte, presenting green fluorescence. TRPV3 staining presented red fluorescence, most of which overlapped with the fluorescence of the K14, which indicated that the TRPV3 was abundantly expressed in the skin keratinocyte. A mean fluorescence intensity was further measured by the Leica microsystem analysis application, and results were shown in FIG. 1B, wherein expression of the TRPV3 in an epidermis of a psoriasis lesion was significantly higher than that of a healthy skin, and * represented that P<0.05.

Embodiment 2

The embodiment is used to illustrate an application of screening a drug for preventing or treating psoriasis with a TRPV3 as a target provided by the present invention.

(1) Mouse Psoriasis Model Induced by Imiquimod

16 C57BL/6 mice, with half male and half female were purchased from the Experimental Animal Center of Nanjing Medical University, wherein weights of the mice ranged from 18 g to 20 g. Back hair of the mice was shaved off, and then the mice were randomly divided into 2 groups (8 mice in each group) according to male and female genders. Before experiment, the mice were placed in a quiet environment kept away from strong light for 3 days to adapt to the environment, a ratio of an illuminating time to a dark time was 1:1, a room temperature was controlled at 25° C., a humidity was 55%, and the mice could eat and drink freely. 62.5 mg of 5% (0.1 g:2 g) imiquimod ointment (Zhuhai United Laboratories Co., Ltd.) was continuously applied to back skins of the mice for 6 days to induce a psoriasis-like lesion, while the same dose of vaseline ointment was given to the control group. The back skins of the mice were photographed and recorded on the 1st, 3rd and 5th days of modeling and skin appearances on the 5th day of modeling were shown in FIG. 2A.

(2) Evaluation on Clinical Symptom of the Mouse Psoriasis Model

The clinical symptom of the mouse psoriasis model was evaluated by a PASI scoring standard from three indicators of erythema, scale and infiltration thickening. The scores ranged from 0 point to 4 points, and a total score was obtained by adding scores of the three indicators. The PASI scoring standard was as follows: 0 point referred to no symptom; 1 point referred to a mild degree; 2 points referred to a moderate degree; 3 points referred to a severe degree; and 4 points referred to an extremely severe degree. The PASI evaluation was conducted daily before the IMQ ointment was applied. Results were shown in FIG. 2B and Table 1. It should be noted that measurement data was represented by mean±standard deviation (mean±SD), and was detected by One-Way ANOVA, wherein in the analysis results, ** represented that $P<0.01$, which was relative to the vaseline group.

Figure 2A:
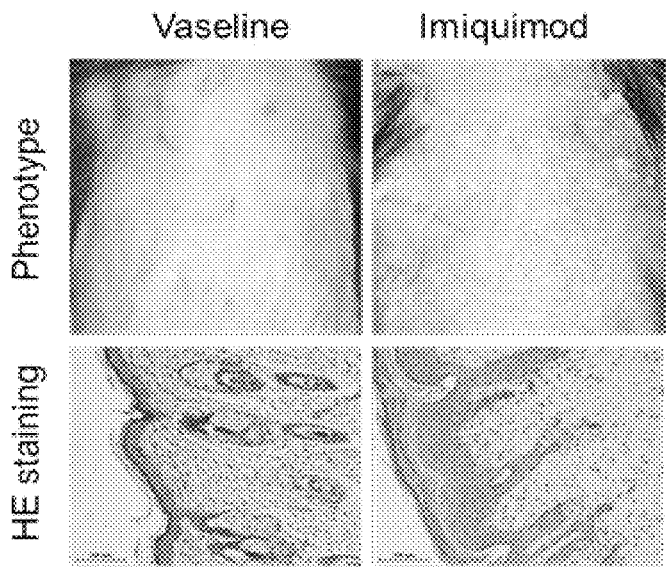
FIG. 2A shows typical appearance and pathological changes of lesion in a mouse psoriasis model induced by 5% IMQ according to an embodiment provided by the present invention.
Figure 2B:
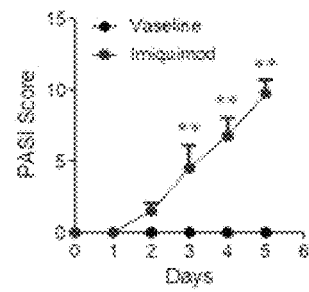
FIG. 2B shows PASI score of the lesion of the mouse psoriasis model induced by 5% IMQ.

Continuous application of imiquimod cream could lead to a psoriasis-like lesion on the back skin of the mouse, which was characterized by such clinical features as erythema, scale and skin thickening, and was significantly different from those of the vaseline group (FIG. 2B and Table 1).

deviation (mean±SD), and was detected by One-Way ANOVA, wherein ** represented that $P<0.01$, which was relative to the vaseline group.

(4) Immunofluorescence Staining on the Skin Paraffin Section of the Mouse

Please referred to Embodiment 1(2) for specific steps, and results were shown in FIG. 3A, wherein a surface marker K14 of a keratinocyte was positive in green, TRPV3 was positive in red, and a cell nucleus was blue. In the epidermal layer, IMQ modeling significantly enhanced a fluorescence intensity of the TRPV3.

(5) mRNA Level of the TRPV3 in the Mouse Psoriasis Model 20 mg of skin tissues were grinded to powder with liquid nitrogen, added with 0.5 mL of Trizol (Vazyme, article number: R401-01), and incubated on ice for 10 minutes. A split product was transferred to a 1.5 mL RNase-free centrifuge tube, added with 100 μL of chloroform, then shaken vigorously for 15 seconds, stood on ice for 2 minutes, and then centrifuged at 4° C. at 12000 rpm for 10 minutes. A water phase on an upper layer was absorbed into a new 1.5 mL RNase-free centrifuge tube, added with the same amount of isopropanol to precipitate RNA, and then centrifuged at 4° C. at 12000 rpm for 10 minutes. A supernatant was discarded, 500 μL of 75% ethyl alcohol prepared with DEPC water was added to wash the RNA precipitate, and then centrifuged at 4° C. at 12000 rpm for 5 minutes. A supernatant was discarded, the RNA precipitate was slightly dried, and the RNA was dissolved with 10 μL of DEPC

TABLE 1

PASI Score of Skin Appearance of Mouse Psoriasis Model Induced by Imiquimod

| Group | Days | | | | |
|---|---|---|---|---|---|
| | 1 | 2 | 3 | 4 | 5 |
| Vaseline | 0.0 ± 0.0 | 0.0 ± 0.0 | 0.0 ± 0.0 | 0.0 ± 0.0 | 0.0 ± 0.0 |
| Imiquimod | 0.0 ± 0.0 | 1.5 ± 0.8 | 4.5 ± 2.2** | 6.8 ± 1.7** | 9.8 ± 1.3** |

Note:
the measurement data was represented by mean ± standard deviation (mean ± SD), and was detected by One-Way ANOVA, wherein in the analysis results,
**represented that P < 0.01, which was relative to the vaseline group.

(3) Histopathological Examination of the Mouse Psoriasis Model

Figure 2C:
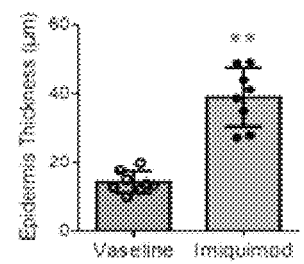
FIG. 2C summaries epidermis thickness of the lesion of the mouse psoriasis model induced by 5% IMQ.

After sacrifice of the mice, skin tissues were collected, fixed with 10% (mass fraction) paraformaldehyde solution, embedded in paraffin, and then subjected to 3 μm slicing and HE staining. An Eclipse Ti inverted microscope (Nikon Corporation, Tokyo, Japan) was used to observe and take a photo at 400-times magnification, and NIS-element BR software (Nikon Corporation, Tokyo, Japan) was used to measure an epidermal thickness of the skin. Six fields of view were randomly selected for each section. Results were shown in FIG. 2A and FIG. 2C. It could be seen from the HE-stained skin tissue section that, at a lesion part of the psoriasis-like sample induced by imiquimod, an stratum spinosum of the skin was significantly thickened, a stratum granulosum of the skin was broken or disappeared, a stratum corneum of the skin was excessively keratinized, and infiltration of an inflammatory cell such as a Langerhans cell was occasionally seen in the epidermal layer of the skin. However, the layers of the skins of the vaseline group presented normal physiological forms, and an epidermal thickness thereof was significantly lower than that of the imiquimod modeling group (FIG. 2A and FIG. 2C). It should be noted that measurement data was represented by mean±standard water. 1 μL of the mixture was subjected to concentration detection by a detection instrument which was Nano-100 ultra-micro spectrophotometer (Hangzhou Aosheng Instrument Co., Ltd., article number: AS-11010). Another 500 ng of the RNA was subjected to a reverse transcription reaction, which was operated according to instructions of HiScript® II One Step RT-PCR Kit (Vazyme, article number: P611-01). A reverse transcription product was stored at −20° C. for later use.

TRPV3 primers (forward primer: 5'-CGGTCACCAA-GACCTCTCCA-3'(SEQ ID NO.:01), and reverse primer: 5'-CGCTCGGACTGTTGGGATTG-3' (SEQ ID NO.:02) were synthesized by Nanjing Springen Biotechnology Co., Ltd. A real-time quantitative PCR reaction was performed in a real-time fluorescence quantitative PCR system (Quant Studio 3, Thermo Fisher Scientific, USA) according to instructions of AceQ qPCR SYBR® Green Master Mix (Vazyme, article number: Q111-01). A reaction system was composed of 1 μL of reverse transcription product, 0.5 μL of 10 μM forward primer, 0.5 μL of 10 μM reverse primer, 8 μL of DEPC water and 10 μL of premixed dye solution, and the mixture was reacted under conditions of pre-denaturation at 95° C. for 10 minutes, denaturation at 94° C. for 30 seconds, and annealing and elongation at 60° C. for 30 seconds (signals were collected once), and the denaturation, the annealing and the elongation were repeated 40 times. Then, the mixture was subjected to a melting curve reaction: maintained at 95° C. for 1 minute, and then maintained at 55° C. for 1 minute, then started to be maintained at a temperature increased by 0.5° C. in each cycle for 13 seconds (signals were collected once), with a total of 81 cycles, and the melting curve reaction was ended when the temperature was increased to 95° C. Data of the real-time quantitative PCR was processed by a $2^{-\Delta\Delta Ct}$ method to reflect an effect of IMQ modeling on expression of the TRPV3 in skin relative to an mRNA transcription level of the vaseline group. Results were shown in FIG. 3B. It should be noted that measurement data was represented by mean±standard deviation (mean±SD), wherein in analysis results, ** represented that P<0.01, which was relative to the vaseline group.

(6) Protein Level of the TRPV3 in the Mouse Psoriasis Model 20 mg of skin tissues were grinded to powder with liquid nitrogen, added with 100 µL of protein lysate, grinded on ice with an electric homogenizer for 20 seconds, and centrifuged at 4° C. and at 12000 rpm for 15 minutes, and then 4 µL of supernatant was used for protein concentration determination. Standard protein and sample protein solutions were prepared according to instructions of a BCA protein concentration determination kit, and a protein standard curve and a sample protein content at a wavelength of 562 nm of a microplate reader were measured. A specific operation process was not elaborated here. 10% separation gel and spacer gel were prepared. The denatured protein sample was vortexed, and centrifuged at 12000 rpm for 5 minutes, and then a pre-dyed protein marker (1 µL) and the protein sample (about 20 µg) were loaded into sample application wells, subjected to electrophoresis at a constant voltage of 80 V for 40 minutes, and then subjected to electrophoresis at an adjusted voltage of 120 V for 60 minutes. The protein was transferred from the gel to a nitrocellulose membrane by a wet method, and was transferred at a constant current of 320 mA for 70 minutes. After the transferring, the nitrocellulose membrane was taken out and immersed in a TBS solution, shaken and washed for 5 minutes, and then shaken and blocked for 1 hour at room temperature with 5% defatted milk powder blocking solution. After the blocking, a TRPV3 antibody (Novus, article number: NBP2-12909) was diluted with a fresh blocking solution at a ratio of 1:1,000, and shaken and incubated overnight at 4° C. After incubation of a primary antibody, the membrane was washed with 1×TBST solution for 4 times, and oscillated at room temperature for 5 minutes each time. Then, the membrane was washed with a TBS solution for 5 minutes. An IRDye® 680RD fluorescence secondary antibody (LI-COR, Lincoln, USA) was prepared with 5% defatted milk powder at a ratio of 1:10,000, and incubated at room temperature in dark for 1 hour. After the incubation of the second antibody, the membrane was washed with 1×TBST for 4 times, and oscillated at room temperature for 5 minutes each time. Then, the membrane was washed with a TBS solution for 5 minutes. The washed nitrocellulose membrane protein was placed facedown on a special glass plate of an Odyssey infrared fluorescence scanning imaging system (LI-COR, Lincoln, USA) to avoid bubble generation. After previewing, appropriate parameters were set, the protein was avoided from overexposure, and developed, as shown in FIG. 3C. Image Studio version 5.2 software (LI-COR, Lincoln, USA) was used to calculate a fluorescence value of a target protein, and results were shown in FIG. 3D. It should be noted that measurement data was represented by mean±standard deviation (mean±SD), wherein in analysis results, ** represented that P<0.01, which was relative to the vaseline group.

It could be seen from results of FIG. 3 that transcription and translation levels of the TRPV3 at the lesion part of the mouse psoriasis model induced by IMQ were significantly higher than those of the normal skin. The results above indicated that the TRPV3 played an important role in the pathological process of psoriasis and might be used as the drug target for preventing and treating skin inflammation such as psoriasis.

Embodiment 3

The embodiment is used to further illustrate an application of developing a drug for preventing or treating psoriasis with a TRPV3 as a target provided by the present invention.

(1) Construction of TRPV3 Knockout Mouse

A CRISPR/Cas9 gene editing technology was used to shear a TRPV3 gene sequence in a fertilized egg of a C57BL/6 strain mouse, resulting in deletion of a 43 bp base. Sequencing results showed that compared with a normal sequence GGACTGCAGTTCC-TATGGCAGCTTCAGCGACGCGGTGCTGGAGCTCTT-CAAGCTCAC CATAGGCCTGGGCGACCTGAA-CATCCAGCAGAACTCCACCTA (SEQ ID NO.:07), a TRPV3 gene sequence of a TRPV3 knockout mouse was GGACTGCAGTTCCT-TCAGCGACGCGG-CGACCT-GAACATCCAG CAGAACTCCACCTA (SEQ ID NO.:08). A heterozygous mouse with deleted 43 bp base of a gene was obtained by hybridization with a wild-type C57BL/6 mouse, and then a heterozygous mouse with deleted TRPV3 alleles was further obtained by heterozygote intercrossing.

(2) Mouse Psoriasis Model Induced by Imiquimod

TRPV3$^{-/-}$ mice and wild-type mice were used to construct mouse psoriasis model induced by imiquimod, wherein a modeling method referred to the description in Embodiment 2 (1). Back skins of the mice were photographed and recorded on the $1^{st}$, $3^{rd}$ and $5^{th}$ days of modeling, and skin appearances on the $5^{th}$ day of modeling were shown in FIG. 4A.

(3) Evaluation on Clinical Symptom of the Mouse Psoriasis Model

Figure 4A:
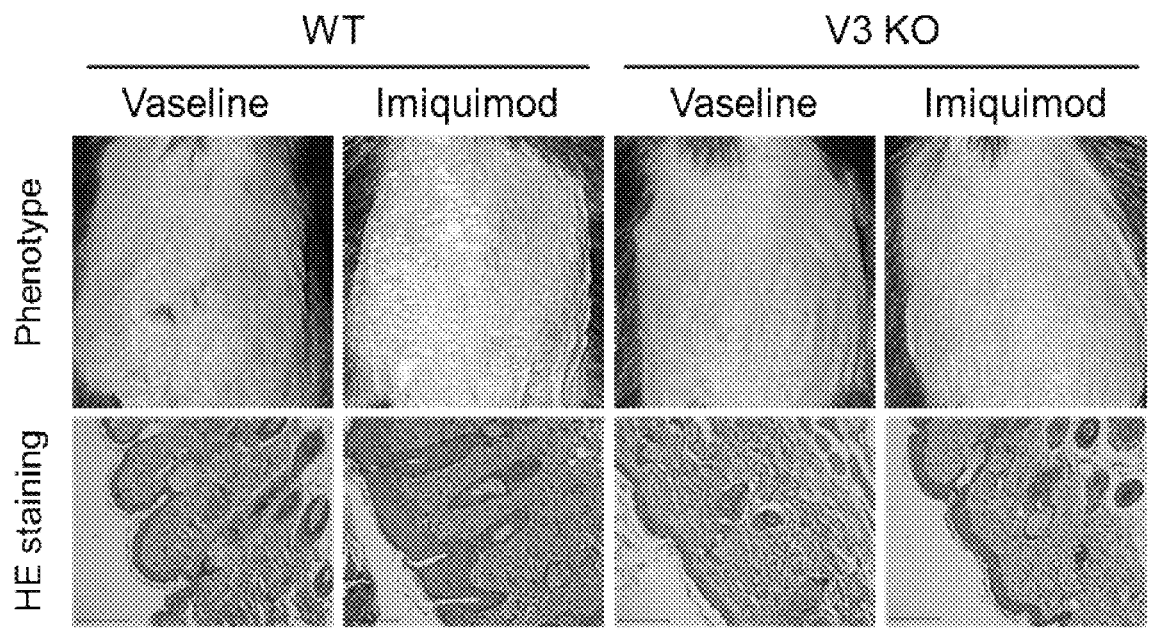
FIG. 4A shows typical appearance and pathological changes of back skins of a wild-type mouse and TRPV3$^{-/-}$ mouse induced by 5% IMQ according to an embodiment provided by the present invention.
Figure 4B:
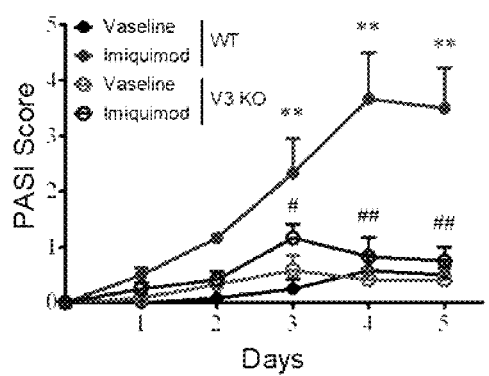
FIG. 4B shows PASI scores of psoriasis-like lesions of the wild-type mice and the TRPV3$^{-/-}$ mice induced by 5% IMQ.

Clinical symptoms of psoriasis-like lesions of the TRPV3$^{-/-}$ mice and the wild-type mice were evaluated by a PASI scoring standard, referring to Embodiment 2 (2), and results were shown in FIG. 4B and Table 2. It should be noted that measurement data was represented by mean±standard deviation (mean±SD), and was detected by One-Way ANOVA, wherein in analysis results, ** represented that P<0.01, which was relative to the wild-type modeling group.

Continuous application of imiquimod cream could lead to a psoriasis-like lesion on the back skin of the wild-type mouse, which was characterized by such clinical features as, and was significantly different from those of the TRPV3 knockout mouse (FIG. 4B and Table 2).

TABLE 2

PASI Scores of Psoriasis-like Lesions of TRPV3 Knockout Mouse and Wild-type Mouse Induced by Imiquimod

| Group | Days | | | | |
|---|---|---|---|---|---|
| | 1 | 2 | 3 | 4 | 5 |
| Wild type | 1.3 ± 1.2 | 2.0 ± 1.0 | 2.3 ± 1.5 | 3.7 ± 1.2 | 4.0 ± 1.0 |
| TRPV3 knockout | 0.3 ± 0.6 | 0.3 ± 0.6 | 0.7 ± 1.2** | 0.7 ± 1.2** | 0.3 ± 0.6** |

Note:
measurement data was represented by mean ± standard deviation (mean ± SD), and was detected by One-Way ANOVA, wherein in analysis results,
**represented that P < 0.01, which was relative to the wild-type modeling group.

(4) Histopathological Examination of the Mouse Psoriasis Model

Figure 4C:
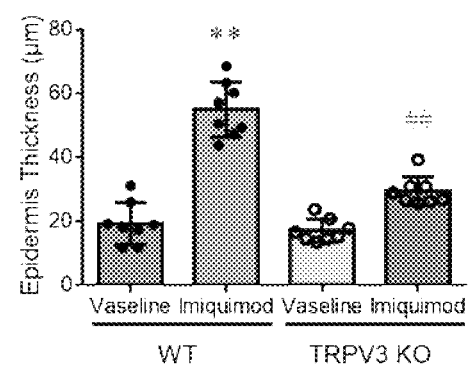
FIG. 4C shows statistics of epidermis thicknesses of the back skins of the wild-type mice and the TRPV3$^{-/-}$ mice induced by 5% IMQ.

Please refer to Embodiment 2 (3) for operation steps. It could be seen from a HE-stained skin tissue section that, at a lesion part of the psoriasis-like sample of the wild-type mouse, an stratum spinosum of the skin was significantly thickened, a stratum granulosum of the skin was broken or disappeared, a stratum corneum of the skin was excessively keratinized, and infiltration of an inflammatory cell such as a Langerhans cell was occasionally seen in an epidermal layer of the skin. However, a stratum spinosum of the skin of the TRPV3$^{-/-}$ mouse was slightly thickened, but a physiological form of each layer was relatively normal, and an epidermal thickness was significantly lower than that of the wild-type mouse modeling group (FIG. 4A and FIG. 4C). Measurement data was represented by mean±standard deviation (mean±SD), and was detected by One-Way ANOVA, and ** represented that P<0.01, which was relative to the wild-type modeling group.

Figure 5A:
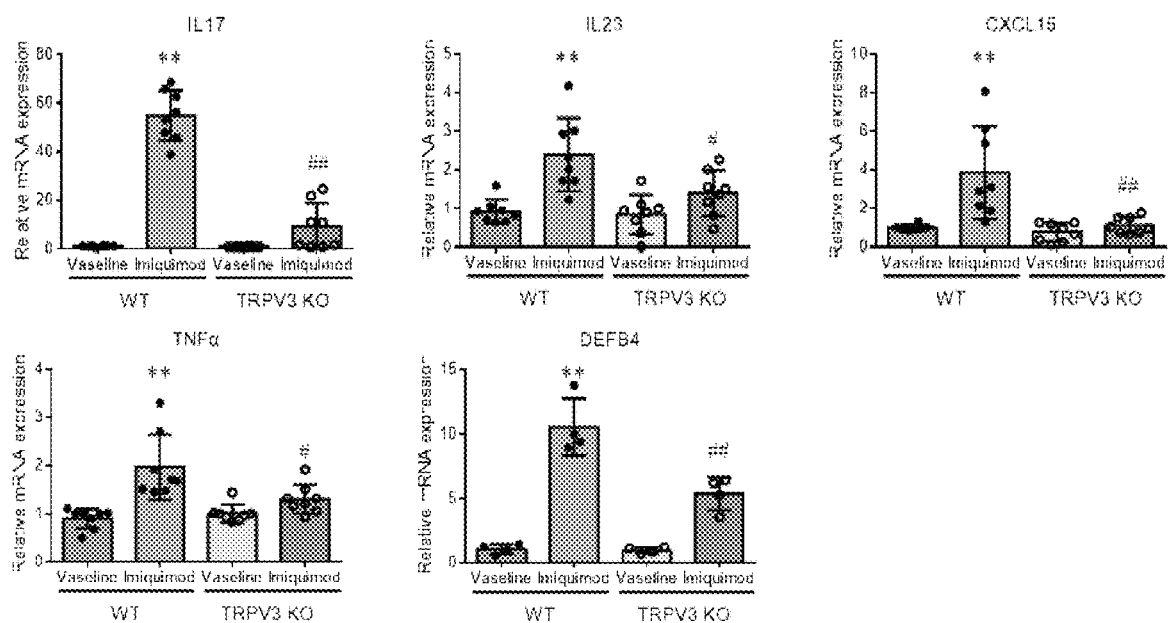
FIG. 5A shows mRNA changes of IL17, IL23, CXCL15, TNFα and DEFB4 in skins of wild-type mice and TRPV3$^{-/-}$ mice after being irritated by 5% IMQ according to an embodiment provided by the present invention.

(5) mRNA Level Detection of Related Inflammatory Factors of the Mouse Psoriasis Model Please refer to Embodiment 2 (5) for operation steps, and specific primers of related inflammatory factors were listed in Table 3. Results of qPCR detection were analyzed by a $2^{-\Delta\Delta Ct}$ method, and the results were shown in FIG. 5A. It should be noted that measurement data was represented by mean±standard deviation (mean±SD), wherein in analysis results, ** represented that P<0.01, which was relative to the wild-type vaseline group; while # represented that P<0.05 and ## represented that P<0.01, which were relative to the wild-type modeling group.

TABLE 3

Primer Table of Psoriasis-Related Inflammatory Factors Derived from Mouse

| Target gene | Forward primer (5'-3') | Reverse primer (5'-3') |
|---|---|---|
| IL6 | GTGTGAAAGCAGCAAAGAG (SEQ ID NO.: 03) | CTCCAAAAGACCAGTGATG (SEQ ID NO.: 04) |
| IL8 | GTCCTTGTTCCACTGTGCCT (SEQ ID NO.: 05) | GCTTCCACATGTCCTCACAA (SEQ ID NO.: 06) |
| IL17 | TTTAACTCCCTTGGCGCAAAA (SEQ ID NO.: 09) | CTTTCCCTCCGCATTGACAC (SEQ ID NO.: 10) |
| IL23 | ATGCTGGATTGCAGAGCAGTA (SEQ ID NO.: 11) | ACGGGGCACATTATTTTTAGTCT (SEQ ID NO.: 12) |
| CXCL15 | TCGAGACCATTTACTGCAACAG (SEQ ID NO.: 13) | CATTGCCGGTGGAAATTCCTT (SEQ ID NO.: 14) |
| TNFα | CCTGTAGCCCACGTCGTAG (SEQ ID NO.: 15) | GGGAGTAGACAAGGTACAACCC (SEQ ID NO.: 16) |
| DEFB4 | CTCCACTTGCAGCCTTTACC (SEQ ID NO.: 17) | TTCATCTTGCTGGTTCTTCGTCT (SEQ ID NO.: 18) |
| IL18 | GACTCTTGCGTCAACTTCAAGG (SEQ ID NO.: 19) | CAGGCTGTCTTTTGTCAACGA (SEQ ID NO.: 20) |

Figure 5B:
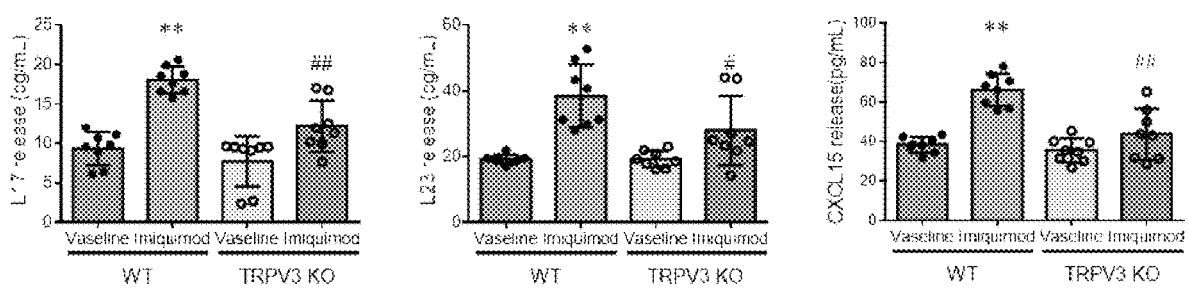
FIG. 5B shows changes of release of IL17, IL23 and CXCL15 in the skins of the wild-type mice and the TRPV3$^{-/-}$ mice after being irritated by 5% IMQ according to the embodiment provided by the present invention.
Figure 6A:
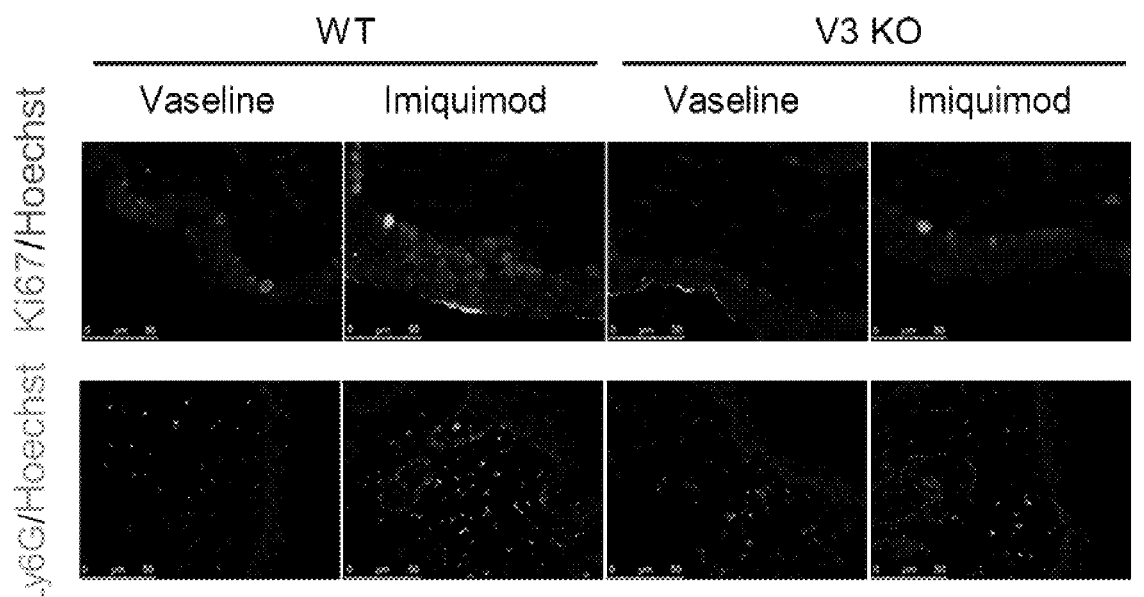
FIG. 6A shows immunofluorescence staining of Ki67 and Ly6G in skins of wild-type mice and a TRPV3$^{-/-}$ mice after being irritated by 5% IMQ according to an embodiment provided by the present invention.
Figure 6B:
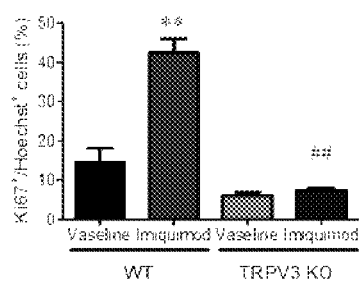
FIG. 6B shows statistics of a proportion of Ki67$^{+}$ cells in the skins of the wild-type mice and the TRPV3$^{-/-}$ mouse after being irritated by 5% IMQ.
Figure 6C:
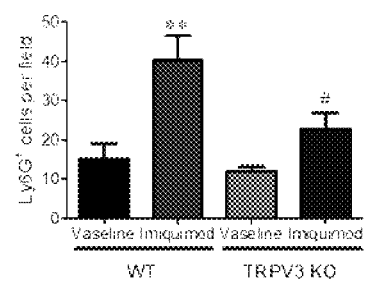
FIG. 6C shows statistics of a proportion of Ly6G$^{+}$ cells in the skins of the wild-type mouse and the TRPV3$^{-/-}$ mouse after being irritated by 5% IMQ.
Figure 6D:
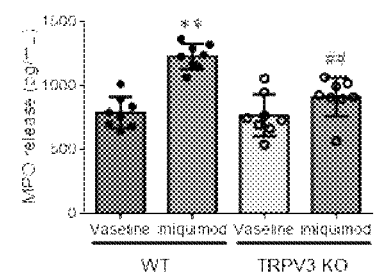
FIG. 6D shows content changes of MPO in the skins of the wild-type mice and the TRPV3$^{-/-}$ mice after being irritated by 5% IMQ.

(6) Content Detection of the Related Inflammatory Factor of the Mouse Psoriasis Model Contents of IL17, IL23, CXCL15 and myeloperoxidase (MPO) in the skin of the mouse were detected by enzyme-linked immunosorbent assay (ELISA), and ELISA kits for various inflammatory factors were all purchased from ELISA Biotechnology Co., Ltd. Specific operation steps were briefly described as follows according to instructions: 50 mg of fresh skin sample was added with 450 μL of PBS (pH=7.2 to 7.4), homogenized on ice, and centrifuged at 5000 rpm for 15 minutes, and then a supernatant was used for detection. A standard substance was diluted according to a proportion, and a blank well, a standard substance well and a well for sample to be detected were set respectively. 50 μL of standard substance was accurately loaded to an ELISA coating plate, and 40 μL of sample diluent was added into the well for sample to be detected firstly, and then added with 10 μL of sample to be detected (a final dilution concentration of the sample was 5 times). The sample was loaded to bottoms of the wells in the ELISA plate without touching walls of the wells to the greatest extent, and then shaken and mixed gently. After sealing the plate with a microplate sealer, the mixture was incubated at 37° C. for 30 minutes. A 30-times concentrated cleaning solution was diluted 30 times with distilled water for later use. The microplate sealer was carefully removed, the liquid was discarded, and the remaining was subjected to spin-drying, and the cleaning solution was fully filled into each well, stood for 30 seconds and then discarded. The steps were repeated for 5 times, and then the mixture was patted dry. 50 μL of ELISA reagent was added into each well, except for the blank well. After sealing the plate with a microplate sealer, the mixture was incubated at 37° C. for 30 minutes. The microplate sealer was carefully removed, the liquid was discarded, and the remaining was subjected to spin-drying, and the cleaning solution was fully filled into each well, stood for 30 seconds and then discarded. The steps were repeated for 5 times, and then the mixture was patted dry. 50 µL of developer A was added into each well firstly, and then then added with 50 µL of developer B, shaken and mixed gently, and then developed in dark at 37° C. for 15 minutes. 50 µL of stop solution was added into each well to stop the reaction (blue turns into yellow at the moment). An absorbance (OD value) of each well was measured sequentially at a wavelength of 450 nm. The measurement should be performed within 15 minutes after the stop solution was added. Results were shown in FIG. 5B. Application of IMQ could induce increase of contents of IL17, IL23 and CXCL15 in the skin of the wild-type mouse, and a difference was significant (** represented that $P<0.01$) relative to a wild-type mouse applied with vaseline. The contents of the three inflammatory factors above in the skin of the TRPV3 knockout mouse applied with IMQ were significantly lower than those of the wild-type mouse applied with IMQ (# represented that $P<0.05$, while ## represented that $P<0.01$). In addition, change of MPO content in the skin of the mouse was similar to those of the three inflammatory factors above, and quantitative results were shown in FIG. 6D.

(7) Immunofluorescence Staining on Skin Paraffin Section of Mouse

Please refer to Embodiment 1 (2) for specific steps. Results were shown in FIG. 6A. A cell proliferation marker Ki67 was positive with green fluorescence (upper), a neutrophil surface marker Ly6G showed green fluorescence (lower), and a cell nucleus was stained with Hoechst and presented blue fluorescence. Quantitative results of numbers of $Ki67^+$ cells and neutrophils were shown in FIG. 6B and FIG. 6C respectively. Measurement data was represented by mean±standard deviation (mean±SD), wherein in analyses results, ** represented that $P<0.01$, which was relative to the wild-type vaseline group; while # represented that $P<0.05$ and ## represented that $P<0.01$, which were relative to the wild-type modeling group.

The results above showed that the deletion of the TRPV3 in the skin could alleviate the psoriasis-like lesion induced by imiquimod. Therefore, the TRPV3 inhibitor or the drug capable of reducing expression of the TRPV3 could be used as the drug for treating psoriasis and other skin diseases, and the target had a good development prospect.

Embodiment 4

The embodiment is used to illustrate an application of Scutellarein as a preferred TRPV3 inhibitor in a drug for preventing or treating psoriasis provided by the present invention.

(1) Obtaining and Culturing of Cell Line Stably Transfecting TRPV3 mTRPV3 plasmids were donated by Professor Jie Zheng from UC Davis. Transfection steps were as follows: HEK-293 cells with a confluence ranging from 70% to 80% and a good growth state were seeded into T-60 small dishes the day before transfection, each small dish contained $4\times10^5$ cells, and the cells were cultured without penicillin/streptomycin overnight at 37° C. in 5% $CO_2$. 10 µL of plasmids (plasmid concentration was 1000 ng/µL) were diluted with 250 µl of DMEM (article number: 12800017, Gibco), and meanwhile, 10 µL of Lipofectamine 2000 (article number: 11668027, Gibco) was diluted into 250 µL of DMEM. Then, the DMEA containing the Lipofectamine 2000 was slowly and dropwise added into the DMEM containing the plasmids, and the mixture was incubated at room temperature for 1 hour, followed by being dropwise added into the T-60 small dishes evenly, transfected for 6 hours, and removed to a 5 mL medium and cultured continuously. After being transfected for 48 hours, the cells were digested and passaged, and 1 mg/mL antibiotic G418 (article number: 11811031, Gibco) (selective medium) was added for pressure screening for about 10 days until the cells grew stably. Monoclone cells were selected by a limiting dilution method: the screened cells were digested and counted, and seeded into a 96-well plate in sequence at densities of $10^4$ cells/well, $10^3$ cells/well, $10^2$ cells/well, 10 cells/well, and 1 cell/well. Under a fluorescence microscope, wells of separate cells with green fluorescence were labeled, and cells amplified from the wells were HEK-293 cells stably transfecting the mTRPV3. The HEK-293 cells stably transfecting the mTRPV3 were cultured in DMEM containing 10% FBS (Fetal Bovine Serum, article number: F2442, Sigma) and 1 mg/mL G418. If the cell density reached 80% to 90%, the cells could be subcultured.

(2) Scutellarein Inhibiting Increase of Intracellular Calcium Concentration Induced by 2-APB on HEK-293 Cells Stably Transfecting TRPV3 mTRPV3-HEK-293 cells were plated into a PDL-coated black-wall bottom-permeable 96-well plate with $2\times10^4$ cells per well. After culturing for 6 hours, the original medium was discarded, and 100 µL of dye containing 4 µM Fluo-4 was added into each well, then the cells were incubated at 37° C. for 60 minutes, and then rinsed with Locke's buffer solution for 5 times. The cell plate was placed in a preheated FLIPR® $^{TETRA}$ (Molecular Devices, Sunnyvale, Calif., USA) at 30° C., and excited at a wavelength of 488 nm, and fluorescence signals were continuously recorded at a sampling frequency of 1 second at a wavelength range of 515 nm to 575 nm. After recording for 60 seconds, a vehicle control, Scutellarein (a final concentration was 10 µM) and ruthenium red (a final concentration was 30 µM) were added, signals were continuously collected for 240 seconds, then 2-APB (a final concentration was 300 µM) was added, and fluorescence signals were continuously collected for 300 seconds. The fluorescence signals were represented by $F/F_0$, wherein F referred to the fluorescence signals at different time points, and $F_0$ refers to a basic fluorescence signal, which was a mean value of the fluorescence signals at the first 5 time points. Results were shown in FIG. 7A, wherein a left arrow indicated the first addition of the solvent control, the Scutellarein or the ruthenium red, and a right arrow indicated the second addition of the 2-APB. With $F/F_0=1$ as a baseline, an area under a curve of a fluorescence intensity change after adding the 2-APB was calculated. Measurement data was represented by mean±standard deviation (mean±SD), wherein in analyses results shown in FIG. 7B, ** represented that $P<0.01$, which was relative to the vehicle control group.

(3) Scutellarein Inhibiting Current of mTRPV3 Channel

HEK-293 cells stably transecting mTRPV3 (mTRPV3-HEK-293) were seeded into T-60 small dishes with a confluence ranging from 20% to 30%, and whole cell current was recorded by a patch clamp amplification system next day. A recording electrode was pulled from a borosilicate glass tube (Sutter Instruments Inc, CA, USA) by a P-1000 Micropipette Puller (Sutter Instrument, Novato, Calif., USA) with an electrode resistance of about 5 MΩ. The recording electrode was filled with an electrode internal solution, which contained 140 mM CsCl, 1 mM MgCl$_2$, 5 mM EGTA, 10 mM HEPES and 0.1 mM CaCl$_2$, with a pH value of 7.20. During recording, the TRPV3-HEK-293 cells were placed in a cell bath solution containing 140 mM NaCl, 5 mM KCl, 2 mM CaCl$_2$, 1 mM MgCl$_2$, 10 mM glucose and 10 mM HEPES, with a pH of 7.40. Current signals were collected at a frequency of 10 kHz and filtered at 2.9 kHz. In order to record the whole-cell current, a cell membrane holding potential was decreased from −60 mV to −100 mV, and maintained for 10 ms, then the cell membrane holding potential was continuously increased from −100 mV to +100 mV within 300 ms, and after maintaining at +100 mV for 10 ms, the voltage was decreased to a holding voltage. Different drugs were administered during patch clamp recording using a rapid solution converter in combination with a nitrogen perfusion system (RSC-200, ALA Scientific Instruments, NY, USA). Each solution was continuously perfused at a place 50 μm from the cells by perfusion microtubules via different pipelines driven by a nitrogen pressure. A solution containing the 2-APB (100 μM) was perfused firstly, and then a solution containing different concentrations of Scutellarein (0.3 μM, 1 μM, 3 μM, 10 μM and 30 μM) and the 2-APB (100 μM) was perfused. Outward currents were recorded, and an inhibitory percentage of the Scutellarein on the outward currents of the 2-APB was calculated using a formula $(I_{2\text{-}APB}-I)/I_{2\text{-}APB}$, wherein I represented an outward current obtained after perfusing a bath solution containing different concentrations of Scutellarein and the 2-APB, and $I_{2\text{-}APB}$ represented a maximum outward current obtained after perfusing the bath solution containing the 2-APB. A 50% inhibitive concentration (IC$_{50}$) of the Scutellarein was calculated by nonlinear fitting, and results were shown in FIG. 7C and FIG. 7D.

Figure 7A:
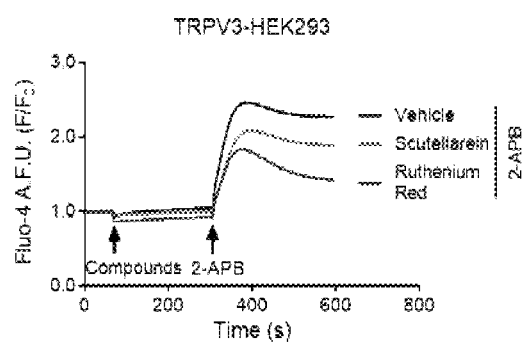
FIG. 7A shows that Scutellarein can inhibit calcium influx induced by 2-APB on a HEK-293 cell stably transfecting a TRPV3 by using an intracellular calcium fluorescence imaging high-throughput screening method in an embodiment provided by the present invention.
Figure 7B:
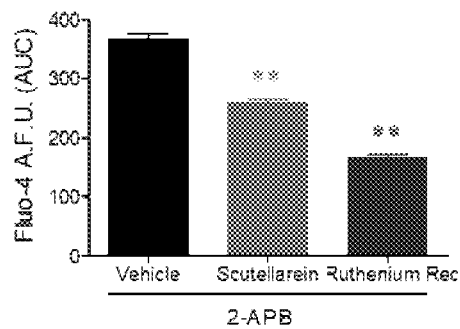
FIG. 7B is a statistical graph of an area under a curve obtained according to FIG. 7A.
Figure 7C:
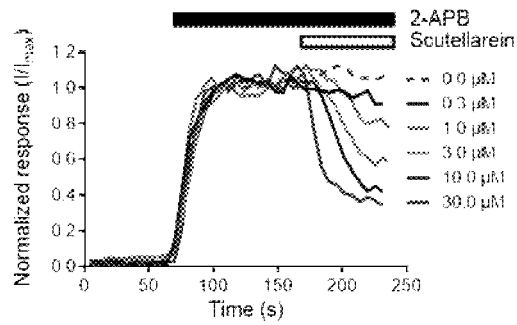
FIG. 7C shows that Scutellarein of different concentrations inhibits a current induced by 2-APB on the HEK-293 cell stably transfecting an mTRPV3 channel.
Figure 7D:
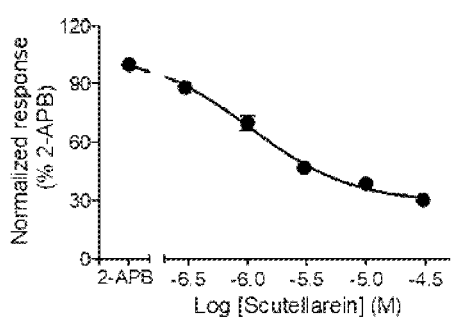
FIG. 7D shows a dose-effect relationship of an inhibitory effect of the Scutellarein on an mTRPV3 current induced by 2-APB

It could be seen from results shown in FIG. 7 that the Scutellarein could inhibit increase of the intracellular calcium concentration induced by the 2-APB on the mTRPV3-HEK-293 cells (FIG. 7A and FIG. 7B). The Scutellarein could inhibit the whole-cell current induced by the 2-APB and had a dose dependence (FIG. 7C). The IC$_{50}$ value of the Scutellarein to the mTRPV3 channel was 1.01 μM (FIG. 7D). The results above indicated that the Scutellarein could inhibit an activity of the mTRPV3 channel and might be used for treating diseases caused by excessive activation of the TRPV3 channel.

Embodiment 5

The embodiment is used to illustrate an application of Scutellarein as a preferred TRPV3 inhibitor in a drug for preventing or treating psoriasis provided by the present invention.

(1) Scutellarein Improving Lesion of Mouse Psoriasis Model Induced by 5% IMQ

C57BL/6 mice, with half male and half female were purchased from the Experimental Animal Center of Nanjing Medical University, wherein weights of the mice ranged from 18 g to 20 g. The C57BL/6 mice were randomly divided into 4 groups (8 mice in each group). Mouse psoriasis models were established as described in Embodiment 2 (1). During modeling, a vehicle control, 0.1% dexamethasone, 0.1% Scutellarein and 0.2% Scutellarein diluted with saline respectively were subcutaneously injected into skins in modeling areas of the mice, with 100 μL each time for twice a day.

Back skins of the mice were photographed and recorded on the 1$^{st}$, 3$^{rd}$ and 5$^{th}$ days after modeling. Clinical symptoms were evaluated by a PASI scoring standard according to Embodiment 2 (2), and results were shown in FIG. 8A, FIG. 8B and Table 4.

Continuous application of imiquimod cream could lead to a psoriasis-like lesion on the back skin of the mouse, which was characterized by such clinical features as erythema, scale and skin thickening. The mice in the vehicle control group suffered the most serious lesion. Subcutaneous injection of dexamethasone or Scutellarein could relieve the psoriasis-like lesion on the back skins of the mice (left in FIG. 8A) and delay occurrence of the lesion induced by imiquimod (FIG. 8B and Table 4). Data shown in FIG. 8B was represented by mean±standard deviation (mean±SD), wherein * represented that P<0.05 and ** represented that P<0.01, which were relative to the vaseline group; while # represented that P<0.05 and represented that P<0.01, which were relative to the model group.

TABLE 4

PASI Score of Skin Appearance of Mouse Psoriasis Model Induced by Imiquimod under Drug Intervention (n = 8)

| Group | Days | | | | |
|---|---|---|---|---|---|
| | 1 | 2 | 3 | 4 | 5 |
| Imiquimod | 0.0 ± 0.0 | 1.0 ± 0.8 | 3.0 ± 2.2 | 4.5 ± 1.7 | 6.5 ± 1.3 |
| Dexamethasone + imiquimod | 0.0 ± 0.0 | 0.3 ± 0.5 | 0.8 ± 0.5** | 1.5 ± 1.0** | 2.3 ± 0.9** |
| 0.1‰ scutellarein + imiquimod | 0.0 ± 0.0 | 0.5 ± 0.6 | 1.8 ± 0.9 | 1.8 ± 1.0** | 3.0 ± 0.8** |
| 0.2‰ scutellarein + imiquimod | 0.0 ± 0.0 | 0.0 ± 0.0 | 0.5 ± 0.6** | 0.8 ± 0.9** | 2.0 ± 1.2** |

Note:
measurement data was represented by mean ± standard deviation (mean ± SD), and was detected by One-Way ANOVA, wherein in analysis results,
**represented that P < 0.01, which was relative to the model group.

Figure 8A:
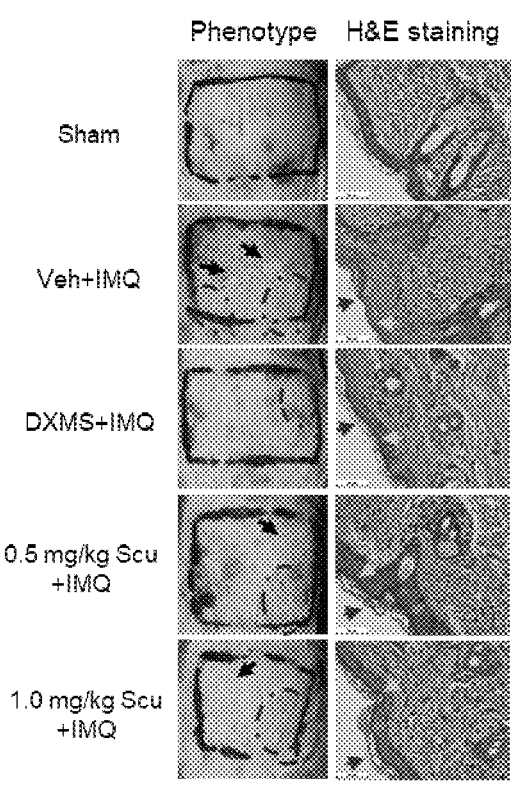
FIG. 8A shows an effect of the Scutellarein on appearance and pathological changes of a mouse psoriasis model induced by 5% IMQ according to a preferred embodiment provided by the present invention.
Figure 8B:
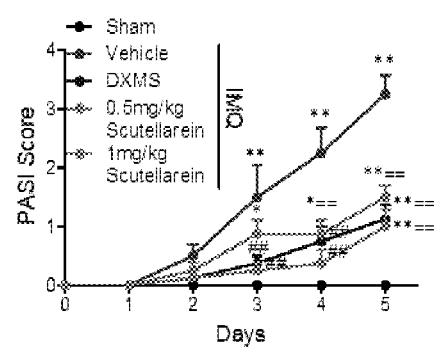
FIG. 8B show an effect of the Scutellarein on an induction process of the mouse psoriasis model.
Figure 8C:
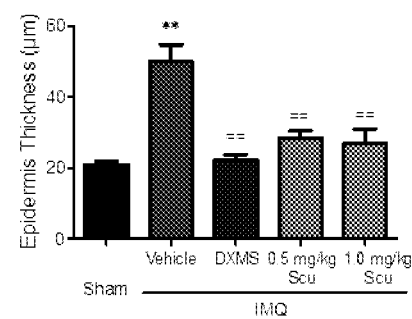
FIG. 8C shows an effect of the Scutellarein on an epidermis thickness of a lesion part of the mouse psoriasis model induced by IMQ.

Histopathological examination of the mouse psoriasis model was conducted as described in Embodiment 2 (3), and results were shown in FIG. 8A (right) and FIG. 8C. It could be seen from a HE-stained skin tissue section that, a stratum spinosum of the skin of the mouse in the vehicle control group was significantly thickened, a stratum granulosum of the skin was broken or disappeared, a stratum corneum of the skin was excessively keratinized, and infiltration of an inflammatory cell such as a Langerhans cell was occasionally seen in an epidermal layer. However, the subcutaneous injection of dexamethasone or Scutellarein could improve the above pathological changes of the skin induced by imiquimod (right in FIG. 8A) and significantly reduce an epidermal thickness at a lesion part of the psoriasis sample (FIG. 8C).

Figure 9G:
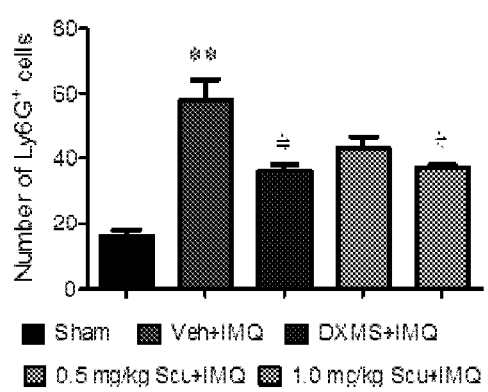
FIG. 9G shows an effect of the Scutellarein on a number of Ly6G$^{+}$ cells at the lesion part of the mouse psoriasis model induced by IMQ.

(2) Scutellarein Reducing mRNA Level of Related Inflammatory Factors of the Mouse Psoriasis Model Please refer to Embodiment 3 (5) for operation steps, and specific primers of related inflammatory factors were listed in Table 3. Results of qPCR detection were processed by a $2^{-\Delta\Delta Ct}$ method, and results were shown in FIGS. 9 A-E. It should be noted that measurement data was represented by mean±standard deviation (mean±SD), wherein in analysis results, ** represented that P<0.01, which was relative to the vaseline group; while # represented that P<0.05 and ## represented that P<0.01, which were relative to the model group.

Figure 9H:
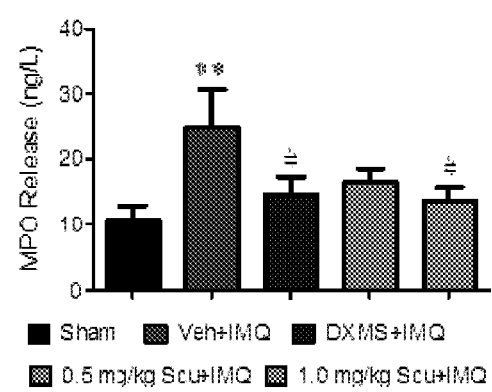
FIG. 9H shows an effect of the Scutellarein on a content of MPO at the lesion part of the mouse psoriasis model induced by IMQ.

(3) Scutellarein Reducing Contents of the Related Inflammatory Factors of the Mouse Psoriasis Model Please refer to Embodiment 3 (6) for operation steps, and quantitative results were shown in FIG. 9F and FIG. 9H. Application of IMQ could induce increase of contents of CXCL15 and MPO in the skin of the wild-type mouse, and compared with the wild-type mouse applied with vaseline, a difference was extremely significant (** represented that P<0.01). In the skin of the mouse of the psoriasis model intervened by Scutellarein, the contents of the two inflammatory factors above were significantly lower than those of a modeling mouse applied with IMQ (# represented that P<0.05, and ## represented that P<0.01).

(4) Scutellarein Reducing Neutrophil Infiltration of the Mouse Psoriasis Model

Please refer to Embodiment 1 (2) for operation steps, wherein five fields of view of each sample were randomly selected, and a number of Ly6G$^+$ cells under the fields of view was recorded. Quantitative results were shown in FIG. 9G, wherein ** represented that P<0.01, which was relative to the vaseline group; and # represented that P<0.05, which was relative to the model group.

It could be seen from the results of the embodiment above that expression of the TRPV3 channel of the present invention was increased at the psoriasis lesion part, and the function deletion of the channel could relieve the psoriasis-like lesion of the mouse induced by imiquimod, which was manifested by relief of symptoms such as thickening of the epidermal layer (keratinocyte proliferation), transcription and release of the related inflammatory factors, the neutrophil infiltration, etc. Therefore, the TRPV3 could become an ideal target for treating psoriasis. Thus, it can be seen that the screening the drug for preventing or treating psoriasis with the TRPV3 as the target according to the present invention has a good development prospect. The HEK-293 cells (TRPV3-HEK-293) stably expressing the TRPV3 can make response to the irritation of the 2-APB, and the cell line can be used for conveniently, rapidly and accurately screening a drug with a regulatory effect on the TRPV3. The Scutellarein discovered by the screening method of the present invention is used as a TRPV3 inhibitor, which can effectively inhibit the activity of the TRPV3, wherein $IC_{50}=1.01$ μM. Further, the Scutellarein can improve the lesion of the mouse psoriasis model induced by 5% IMQ, and obviously reduce transcription and secretion of the related inflammatory factors, and the neutrophil infiltration. Therefore, the Scutellarein is a drug capable of preventing or treating psoriasis, and further, the Scutellarein can treat other diseases caused by function enhancement of the TRPV3.

The preferred embodiments of the present invention are described in detail above with reference to the drawings. However, the present invention is not limited to the specific details in the embodiments above. Various equivalent transformations can be made to the technical solutions of the present invention within the scope of the technical concept of the present invention, and these equivalent transformations shall all fall within the protection scope of the present invention. In addition, it should be noted that various specific technical features described in the specific embodiments above can be combined in any suitable way in case of no contradiction. In order to avoid unnecessary repetition, various possible combinations will not be described separately in the present invention.

In addition, any combination can be made among various embodiments of the present invention without deviating from the idea of the present invention, and should also be regarded as the disclosure of the present invention.

What is claimed is:

1. A method for screening a drug for treating a transient receptor potential cation channel (TRPV3)-related psoriasis comprising the following steps: culturing a cell line expressing the TRPV3, adding Fluo-4, adding a test drug and 2-aminoethoxybiphenylborate (2-APB), recording a fluorescence signal at a wavelength between 515 nm and 575 nm as a basic fluorescence signal when excited at a wavelength of 488 nm, adding the 2-APB, recording the fluorescence signal as a response fluorescence signal, the test drug is a candidate drug for treating the transient receptor potential cation channel (TRPV3)-related psoriasis when a value of the response fluorescence signal is bigger than that of the basic fluorescence signal.

2. The method according to claim 1, wherein the cell line expressing TRPV3 is prepared by transfecting mTRPV3 plasmid into HEK-293 cell; wherein the mTRPV3 plasmid comprises a murine TRPV3 cDNA that is controlled by an eukaryotic promotor.

* * * * *